United States Patent [19]

Meyer

[11] Patent Number: 4,630,924

[45] Date of Patent: Dec. 23, 1986

[54] CONICAL DC PLASMA EMISSION SOURCE

[75] Inventor: Gerhard A. Meyer, Midland, Mich.

[73] Assignee: The Dow Chemical Company, Midland, Mich.

[21] Appl. No.: 760,182

[22] Filed: Jul. 29, 1985

[51] Int. Cl.$^4$ ............................................. G01N 21/73
[52] U.S. Cl. .................... 356/316; 219/121 P; 315/111.21
[58] Field of Search ............... 356/316, 313; 315/111.01, 111.21; 219/121 P, 121 PM, 121 PR, 121 PY, 121 PV

[56] References Cited

U.S. PATENT DOCUMENTS

| | | |
|---|---|---|
| 2,964,678 | 12/1960 | Reid . |
| 3,517,188 | 6/1970 | Sullivan et al. . |
| 3,596,128 | 7/1971 | Elliott . |
| 3,606,540 | 9/1971 | Williams et al. . |
| 3,612,686 | 10/1971 | Braman et al. . |
| 3,714,390 | 1/1973 | Foex et al. . |
| 3,798,408 | 3/1974 | Foex et al. . |
| 3,802,782 | 2/1974 | Natelson . |
| 3,931,542 | 1/1976 | Sheer et al. ............ 219/121 P |
| 3,989,512 | 11/1976 | Sayce ..................... 219/121 P |
| 4,009,413 | 2/1977 | Elliott et al. ............ 219/121 P |
| 4,013,867 | 3/1977 | Fey ......................... 219/121 P |
| 4,147,957 | 4/1979 | Hildebrand ............ 356/316 |
| 4,300,834 | 11/1981 | Demers et al. ......... 356/316 |
| 4,322,165 | 3/1982 | Ellebracht et al. .... 356/316 |
| 4,341,947 | 7/1982 | Komura et al. ........ 219/121 P |
| 4,432,644 | 2/1984 | Demers et al. ......... 356/316 |
| 4,517,495 | 5/1985 | Piepmeier .............. 315/111.21 |

FOREIGN PATENT DOCUMENTS

| | | | |
|---|---|---|---|
| 452725 | 5/1968 | Switzerland ............ 315/111.21 |
| 1035430 | 8/1983 | U.S.S.R. .................. 356/313 |

Primary Examiner—F. L. Evans

[57] ABSTRACT

A DCP spectrometer emission source for creating a conical high temperature plasma through which an aerosol suspended sample is able to penetrate which generally includes at least three D.C. powered electrodes, a base structure for circumferentially spacing the electrodes about a central axis, and an introduction conduit associated with the central axis for injecting the aerosol sample stream into the conical shaped plasma created by the electrodes. The base structure circumferentially spaces the electrodes about the central axis such that the longitudinal axes of the electrodes converge radially toward the central axis at an acute angle to the central axis. Each of the electrodes has an electrode member and a conduit for conveying an ionizable gas passed the electrode members. The electrode members are also connected to a source of D.C. electrical power such that two of the electrode members have the same polarity and the third electrode member has the opposite polarity.

19 Claims, 6 Drawing Figures

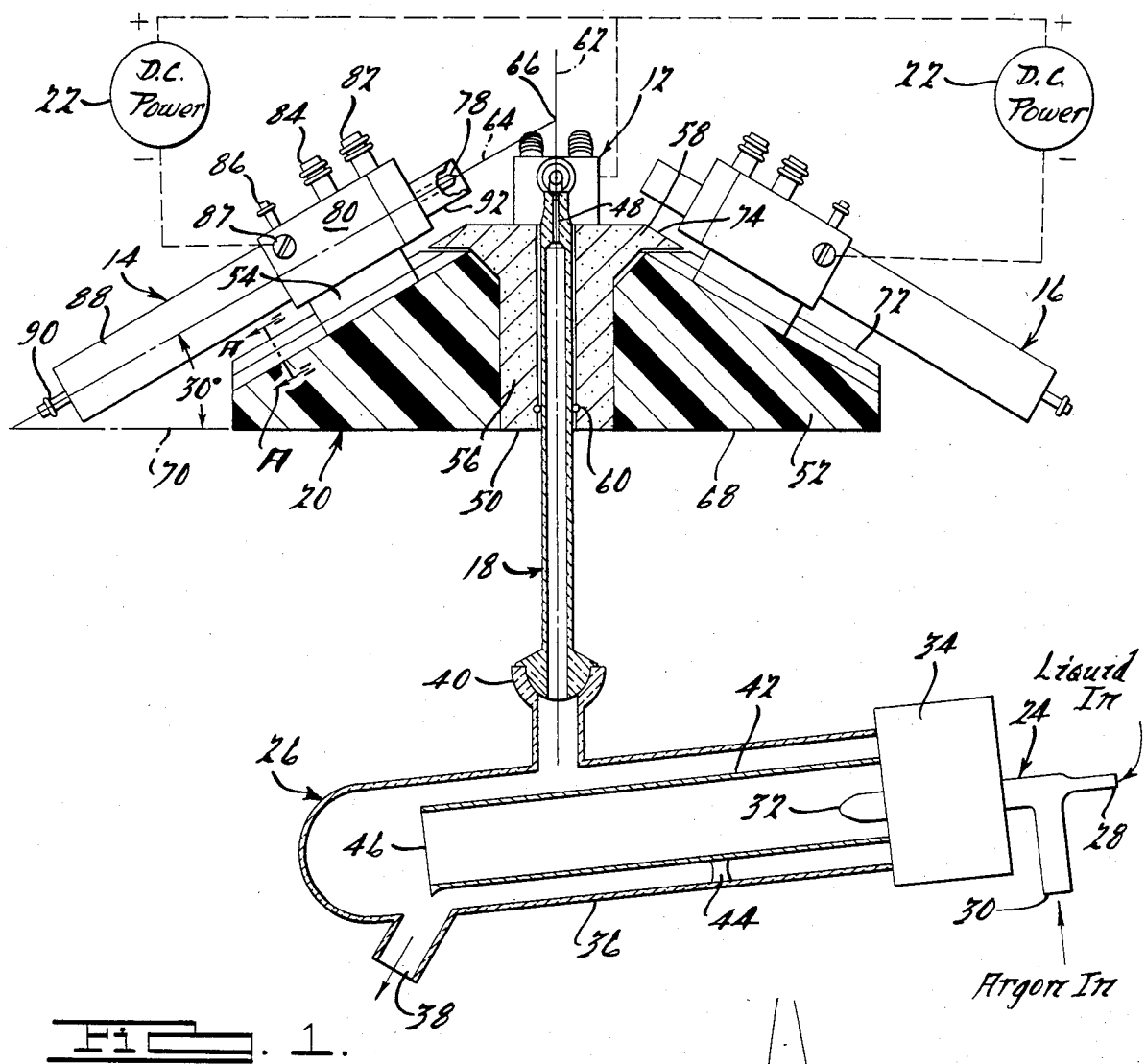
FIG. 1.
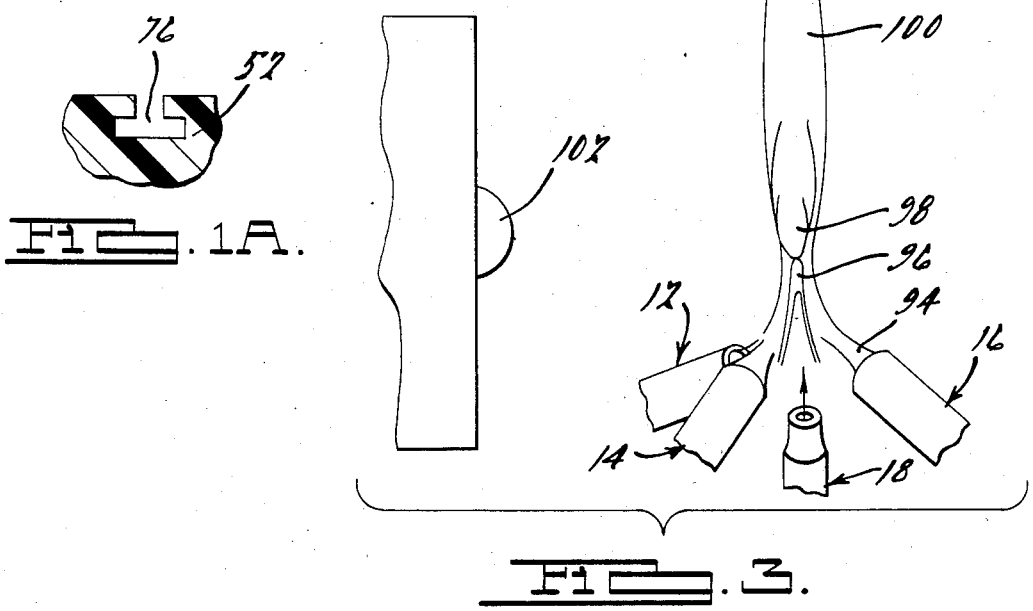
FIG. 1A.
FIG. 3.

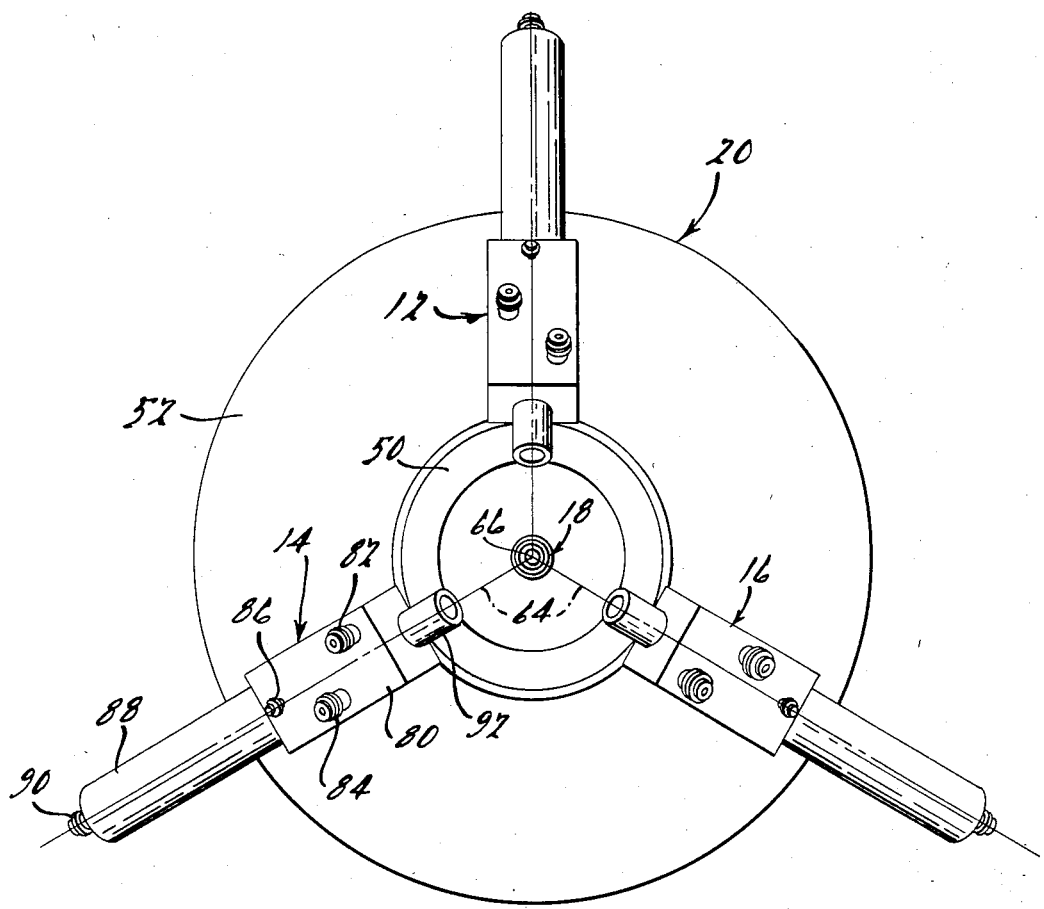
FIG. 2.
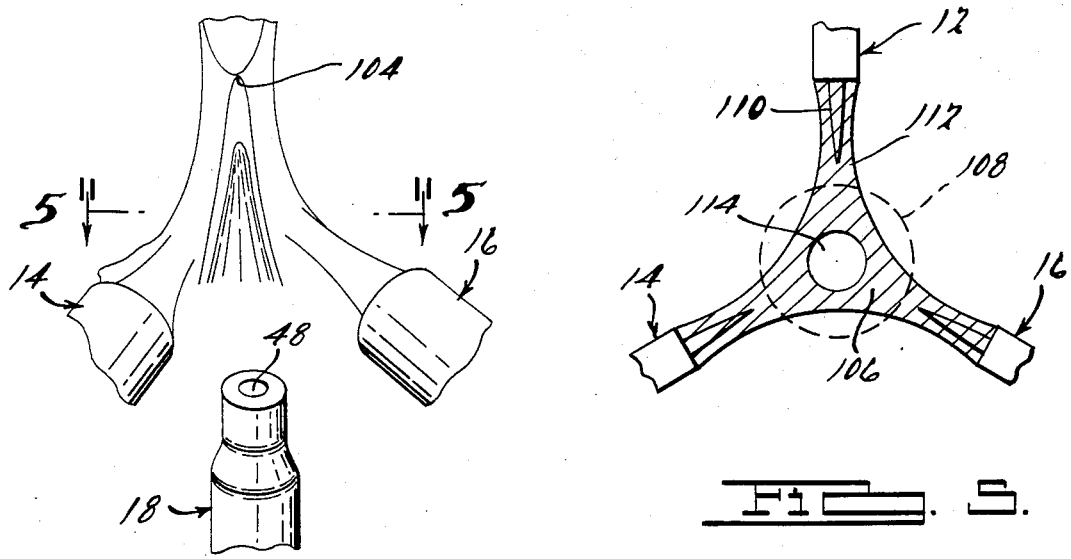
FIG. 4.
FIG. 3.

CONICAL DC PLASMA EMISSION SOURCE

BACKGROUND OF THE INVENTION

The present invention generally relates to optical emission spectrochemical analysis, and particularly to an assembly for creating the high temperature plasma required for spectrochemical analysis of a sample.

In optical emission spectrochemical analysis, a high temperature plasma is used to dissociate the molecular bonds of the sample. The plasma is an ionized inert gas, such as argon. The atomization of the sample by contact with the plasma will cause an excitation of the dissociated atoms to the point where an optically detectable emission is generated. The wavelength and intensity of this emission is indicative of the type and concentration of the atomic elements contained in the sample.

There are at least two known techniques for creating the necessary high temperature plasma. The first technique is referred to as an inductively coupled plasma (ICP), because an induction coil powered from a high frequency alternating current (A.C.) source is used to create the plasma. The other technique is referred to as a direct current plasma (DCP), because the plasma is created by an arc across electrically opposing electrodes which are powered from a direct current (D.C.) source.

One of the distinctions between ICP spectrometers and prior DCP spectrometers relates to the way that the sample interacts with the plasma. In ICP spectrometers, the sample is made to pass directly through the middle of the plasma. Whereas, in prior DCP spectrometers, the sample contacts the plasma, but does not penetrate the plasma. As a result of the sample penetration in ICP spectrometers, sample decomposition is more efficient and a higher analytical sensitivity can be achieved.

Additionally, the lack of sample penetration in prior DCP spectrometers also leads to significant corrosion problems in a relatively short period of time. This is because when the sample stream encounters the plasma, the generally corrosive aerosol vapors from the sample steam spray outwardly from the plasma, and the proximity of the anode to the plasma makes it particularly vulnerable to corrosion. This corrosion significantly increases the maintenance costs associated with the electrode assembly of these prior DCP spectrometers. A discussion of the plasma jets for prior DCP spectrometers may be found in the Hildebrand U.S. Pat. No. 4,147,957, and the Elliott et al U.S. Pat. No. 4,009,413.

Accordingly, it is a principal object of the present invention to obtain the analytical advantages of an ICP spectrometer in a DCP spectrometer using a emission source design which also overcomes the corrosion problems associated with prior DCP spectrometers.

It is a more specific object of the present invention to provide a DCP spectrometer emission source which traps the aerosol sample stream and forces it through the plasma.

It is another object of the present invention to provide a DCP spectrometer emission source which creates a plasma having a generally upwardly converging conical shape when viewed from its lower extremity, so that the aerosol sample will be captured in this cone and drawn up through the plasma.

It is an additional object of the present invention to provide a plasma penetrating emission source which can be retro-fitted into existing DCP spectrometers.

It is a further object of the present invention to provide a DCP spectrometer emission source which provides an ionic emission analytical zone that is well isolated from the atomic analytical zone, with both zones in turn well isolated from the highly intense plasma current trains.

It is yet another object of the present invention to provide a DCP spectrometer emission source which provides for analytical zones of increase size for facilitating enhanced optical analysis by the spectrometer.

It is yet a further object of the present invention to provide a DCP spectrometer emission source which efficiently utilizes the plasma energy in desolvating and exciting the sample stream presented to it.

It is yet an additional object of the present invention to provide a DCP spectrometer emission source which can tolerate high solid sample solutions in analyzing for trace elements.

It is still another object of the present invention to provide a DCP spectrometer emission source which creates a highly stable plasma which permits increased analytical sensitivity.

SUMMARY OF THE INVENTION

To achieve the foregoing objectives, the present invention provides a DCP spectrometer emission source for creating a conical high temperature plasma through which an aerosol suspended sample is able to penetrate. This emission source generally includes at least three D.C. powered electrodes, a base structure for circumferentially spacing the electrodes about a central axis, and an introduction conduit associated with the central axis for injecting the aerosol sample stream into the conical shaped plasma created by the electrodes. The base structure circumferentially spaces the electrodes about the central axis such that the longitudinal axes of the electrodes converge readily toward the central axis at an acute angle to a plane which is perpendicular to the central axis. Each of the electrodes has an electrode member and a conduit for conveying an ionizable gas passed the electrode members. The electrode members are also connected to a source of D.C. electrical power such that two of the electrode members have the same polarity and the third electrode member has the opposite polarity.

With the above-identified electrode assembly configuration, the high temperature plasma created by the D.C. powered electrodes will have a generally conical shape suitable for trapping the aerosol sample stream and forcing it to pass up through the center of the plasma. Thus, it will be appreciated that the position of the electrodes both create and shape the form of the plasma. The size of the sample introduction conduit opening and the relative placement of this conduit opening also assist in forcing the aerosol sample stream through the plasma by imparting a high velocity to the sample stream and directing the narrow sample stream toward the apex of the plasma cone.

Additionally, this electrode configuration provides an efficient use of the D.C. electrical energy use to create the plasma, since substantially all of the sample solution in the aerosol stream is desolvated and excited by the plasma. This sample penetration also provides distinct and separate ionic and atomic emission analytical zones which are sufficiently isolated so as to be easily viewed by the spectrometer's optical detection system.

Another advantage of the DCP spectrometer emission source according to the present invention is that a common base structure is provided which supports all of the electrodes and the introduction conduit or tube. This provides a very compact arrangement which also eliminates the need for the physical movement of one or more of the electrode housings with its associated cooling and gas conduits in order for the plasma to be ignited. Rather, it is only necessary for the electrode members themselves to be temporally projected for the ignition, with all of the associated electrode housing hardware remaining in their optimally defined stationary positions.

Additional advantages and features of the present invention will become apparent from a reading of the detailed description of the preferred embodiment which makes reference to the following set of drawings in which:

BRIEF DESCRIPTION OF THE DRAWINGS

FIG. 1 is a side elevation view, partially in cross-section, of a DCP spectrometer emission source according to the present invention.

FIG. 1A is a cross-sectional view of a portion of the base structure for the emission source shown in FIG. 1, taken generally along lines A—A.

FIG. 2 is a top elevation view of the emission source shown in FIG. 1.

FIG. 3 is a diagrammatic perspective view of the sample penetrating plasma created by the emission source shown in FIGS. 1 and 2.

FIG. 4 is an enlarged view of the plasma shown in FIG. 3, which particularly illustrates the conical shape of the plasma.

FIG. 5 is a cross-sectional view of the plasma shown in FIG. 4, taken generally along lines B—B.

DETAILED DESCRIPTION OF THE PREFERRED EMBODIMENT

Referring to FIG. 1, a DCP spectrometer emission source 10 according to the present invention is shown. The emission source 10 generally comprises a cathode electrode 12, a pair of anode electrodes 14 and 16, an introduction tube 18, and a base structure 20. The base structure 20 is used to both support and align the electrodes 12-16 and the introduction tube 18. The electrodes 12-16 are connected to one or more sources 22 of D.C. (direct current) electrical power in the polarities shown in FIG. 1. The D.C. powered electrodes 12-16 are used to create a high temperature plasma, and the position of these electrodes is selected to give the underside of the plasma a generally conical shape, as will be more fully discussed below.

The introduction tube 18 is used to inject an aerosol sample stream into the generally conical underside of the plasma with a sufficient velocity to enable the sample stream to penetrate the plasma. Specifically, the combination of the sample introduction means with the electrode positions and polarities enables the entirety or substantially the entirety of the aerosol sample stream to be captured in the conical underside of the plasma and forced through the plasma. Thus, it will be appreciated that the typically corrosive aerosol vapors are prevented from spraying outwardly toward the electrodes 12–16 and corroding the electrodes and/or the other hardware associated with the spectrometer emission source.

The sample introduction means according to the present invention includes the introduction tube 18, a nebulizer 24, and a spray chamber 26. The nebulizer 24 includes a liquid inlet port 28, gas inlet port 30, and an aspirator outlet port 32. A suitable carrier gas, such as argon, is injected into the gas inlet port 30 at a flow rate which will cause a steady stream of a liquid containing the sample to be spectrochemically analyzed to be drawn by siphon action into the liquid inlet port 28. The carrier gas will then aspirate the liquid and form an aerosol sample stream.

The nebulizer 24 is connected to the spray chamber 26 through a plastic nebulizer block 34. The spray chamber 26 includes a glass housing 36 having a drain opening 38 and a ball joint outlet port 40, and an elongated cylinder 42 which is concentrically disposed in the housing 36. The cylinder 42 is supported by neck portion 44, and is open at end 46. The cylinder 42 directs excess liquid from the nebulizer 24 to the drain opening 38, and permits a fine aerosol sample stream spray to flow to the ball joint outlet port 40. The bottom portion of the introduction tube 18 is formed to be complimentary in shape to the ball joint outlet port 40 of the spray chamber 26 so as to facilitate a gas tight seal between the introduction tube 24 and the spray chamber 26.

In one embodiment according to the present invention, the introduction tube is a moel 5694-G16 quartz tube manufactured by Thomas Scientific. Similarly, the nebulizer 24 is a model T-230-A1 nebulizer manufactured by Meinhart Industries, Inc., and the spray chamber 26 is barrel-type spray chamber model SC manufactured by Precision Glass Blowing of Colorado. All three of these specific components have been used in some ICP prior spectrometer models, and may be advantageously employed in a DCP spectrometer emission source according to the present invention. However, it should be understood that other suitable components may be employed in the appropriate application. For example, it is preferred that the introduction tube 18 be formed with a relatively small opening or orifice 48 (i.e., 1–2 mm) for creating a fine, narrow and high velocity aerosol sample stream, and directing this sample stream toward the apex or vertex of the conical underside of the plasma. This type of sample stream will assist in capturing the sample stream within the cone of the plasma and forcing it into and through the body of the plasma. The orifice 48 of the introduction tube 18 may be disposed as close to the concial shaped plasma as possible without causing undue heating to the tube.

The introduction tube 18 is supported and vertically aligned by the base structure 20, which supports and aligns the electrodes 12–16. The base structure 20 is generally circular, and includes a central sleeve section 50, and an outer platform section 52. Each of the electrodes 12–16 also include a bracket 54 for mounting the electrodes to the platform section 52 of the base structure 20. The central sleeve section 50 is comprised of a vertically extending neck portion 56, and radially outwardly extending shoulder on top portion 58. The central sleeve section 50 is formed with a vertical bore for receiving the introduction tube 18, and at least one elastomeric ring 60 is positioned in this bore between the central sleeve section and the introduction tube.

FIG. 1 also shows a generally vertical central axis 62 which extends through the center of the introduction tube 18. As may be seen in both FIGS. 1 and 2, the central axis 62 provides the focal point for the electrodes 12-16. Specifically, each of the longitudinal axes 64 of the electrodes 12-16 are aligned with the central axis 62 such that they all converge and join together at a point 66. As will be readily appreciated from FIG. 1, the base structure 20 provides certain angles between these axes which will be explained below. Additionally, it should be noted that the flat bottom 68 of the base structure also defines a generally horizontal plane which extends at a perpendicular angle to the central axis 62. While the bottom 68 of the base structure 20 may have any suitable shape, this particular base structure does provide a plane which may be used as a reference in describing the angle between the central axis 62 and the longitudinal axes of the electrodes 12-16.

As may be best seen from FIG. 2, the electrodes 12-16 are mounted to the base structure 20 such that they are circumferentially spaced about the central axis 62. In one embodiment according to the present invention, the electrodes 12-16 are equally spaced from each other. Accordingly, each of the longitudinal axes 64 of the electrodes 12-16 are separated by a 120° angle with respect to the point 66. While the electrodes 12-186 may be separated from each other by unequal angles, it should be understood that spacing between the electrodes must be such as to create a plasma having a generally conical shape at its lower extremity. Accordingly, it is preferred that the angles between the electrodes 12-16 be set so as to assist in creating a plasma with a conical underside of sufficient uninterrupted depth as to capture all or substantially all of the aerosol sample stream.

It should also be understood that more than three electrodes may be provided in a DCP spectrometer emission source according to the present invention. Three is the minimum number of appropriately positioned electrodes or plasma current train sources required to form a plasma having a generally conical shape at its lower extremity. Thus, more than three electrodes may be used as desired, for reasons such as to enhance the uniformity of the plasma's conical shape. With respect to the elecrode polarities, the additional electrodes could be either cathodes or anodes. Accordingly, it should also be appreciated that the electrode polarities shown in FIGS. 1 and 2 may be reversed, such that there are two cathodes and one anode. However, it is generally preferred that the number of anode electrodes exceed the number of cathode electrodes when an odd number of electrodes is provided, as cathode electrodes are usually constructed with electrode members which can withstand higher temperatures than the electrode members of anode electrodes.

The base structure 20 is constructed to position the electrode members 12-16 at an upturned angle with respect to a horizontal plane, such as plane 70 shown in FIG. 1. In the embodiment of FIG. 1, the electrodes 12-16 are mounted to the base structure 20 such that the longitudinal axes 64 of the electrodes form an approximately 30° angle with respect to the horizontal plane 70. With this angular position, the longitudnal axes 64 of the electrodes also form an approximately 60° angle with respect to the central axis 62.

As in the case of the angular separation between the electrodes 12-16, the angular orientation between the electrodes and a vertical or horizontal reference axis/plane may be suitably varied in the appropriate application. The principal limitation in this regard is the ability to create a plasma having a generally conical shape into which an aerosol sample stream may be injected and trapped. Ultimately, the conical shape of the plasma is dependent upon the combination of the angular spacing between the electrodes 12-16, the angular orientation of the electrodes with respect to a vertical/horizontal reference, the distance between the electrodes and the central axis 62, and to some extent the flow rate of the ionizable gas necessary to create the plasma. Thus, while it is preferred that the angle between the longitudinal axes 64 of the electrodes 12-16 and the horizontal plane be an acute angle between 15° l and 60°, other suitable angles outside of this range may permit a conical shaped plasma to be formed by providing the appropriate dimensions for the other considerations identified above.

In order for the electrodes 12-16 to be positioned at an upward angle, the outer platform 52 of the base structure 20 is formed with a sloped surface 72 that is used for mounting the electrodes to the base structure. In the embodiment of FIG. 1, the sloped surface 72 is formed at a 30° angle with respect to the horizontal plane 70. FIG. 1 also shows that the central sleeve section 50 of the base structure 20 includes a sloped surface 72 which follows the angle of the sloped surface 72.

While FIG. 1 shows that the base structure 20 as being comprised of separate sleeve and platform sections, it should be understood that the base structure may be comprised of a single integral body. In the embodiment of FIG. 1, the central sleeve section 50 is constructed from a plastic material which is more temperature resistant than the platform section 52. Specifically, the central sleeve section is constructed from a glass filled plastic known as Teflon (a DuPont trademark), while the platform section 52 is constructed from Kel-F plastic. However, it should be understood that other suitable materials may be used in the appropriate application. Additionally, while the base structure could be comprised of an assembled or integral framework, it should be appreciated that the base structure 20 of FIG. 1 provides a very compact, stable and inexpensive structure for supporting and aligning the electrodes 12-18 and the introduction tube 18. It should also be noted that the source 10 could be enclosed in a suitable glass or quartz housing which is purged with argon to reduce or prevent air from becoming entrained in the plasma.

FIG. 1A shows that a channel shaped track 76 is formed in the platform section 52 of the base structure 20 for mounting each of the electrodes 12-16. Each of the electrode mounting brackets 54 are also formed with a bottom rail which is complimentary in shape to the shape of the track 76, so that the brackets may slide into and along the track until the proper stationary positions for the electrodes have been reached. The position of the brackets 54 along the tracks 76 may then be fixed by suitable plugs, pins or the like. While the brackets 54 could be welded into position, it is preferred that a detachable securing means be employed in order to facilitate maintenance of the electrodes. In order to anchor the brackets 54 to the electrodes 12-16, one or more bolts or other suitable securing means may be employed. The brackets themselves may be made from any relatively heat resistant material, such as Kel-F or Teflon plastic. Additionally, while FIG. 1 shows that the brackets 54 are formed in the shape of blocks, other suitable shapes and constructions may also be employed in the appropriate application.

The electrodes 12-16 generally comprises a graphite or thoriated tungsten electrode member 78 and a metal electrode housing 80. The electrode housing 80 includes an inlet port 82 and an outlet port 84 for the cooling water, an ionizable gas inlet port 86, an electrical connector 87, a pneumatic cylinder 88, and an electrode member positioning gas inlet port 90. Due to the high temperatures involved in creating a plasma, a constant flow of water or some other cooling fluid is generally provided through the electrode housing 80. Each of the pneumatic cylinders 88 are responsive to the gas pressure at the inlet ports 90 to either leave the electrode members 78 in their retracted operative position shown in FIG. 1, or project the electrodes into a temporary ignition position used to initially create the plasma.

In the ignition position, the tips of the electrode members 78 for each of the electrodes 12–16 will generally meet at the point 66. In order to create a plasma, an ionizable gas stream will be injected into the inlet ports 86, and D.C. electrical power will be supplied to the electrical connectors 87 in the appropriate polarities. An electrical arc will be created across the small gap separating the tips of the electrode members 78 which will ignite or ionize the gas flowing passed the electrode members, thereby create the plasma. The electrode members may then be retracted to the operating position shown in FIG. 1, where the tips of the electrode members 78 will all lie in a horizontally disposed plane. It should be appreciated that the electrodes 12–16 could be separated to create a larger plasma body and that a graphite rod or other suitable means could be used to make the initial electrical connection between the electrodes for ignition purposes.

It should also be noted that the electrode housing 80 includes a ceramic sleeve or conduit 92 which is in communication with the inlet port 86 for directing the ionizable gas flow along a portion of the electrode member 78. The ionizable gas may be any suitable gas such as argon. Additionally, the gas injected into inlet port 90 of the pneumatic cylinder 88 and the gas injected into the inlet port 30 of the nebulizer 24 may also conveniently be argon as well.

In one embodiment according to the present invention, the electrodes 12–16 are model Spectrajet III electrodes manufactured by Spectrametrics, Inc. While these specific electrodes are used in commercial DCP spectrometers marketed by SpectraMetrics, it should be appreciated that other suitable electrode constructions or D.C. powered sources of an ionized gas plasma stream may be employed in a DCP spectrometer emission source according to the present invention.

Referring to FIG. 3, a diagrammatic representation of a conical plasma formed in accordance with the present invention is shown. As illustrated in this Figure, the plasma created by the electrodes 12–16 combine with the aerosol sample stream from the introduction tube to provide several distinct zones. In this regard, reference numeral 94 generally designates the plasma current train provided by the stream of ionized gas flowing from each of the electrodes 12–16. Reference numeral 96 generally designates the plume from the injected sample which provides an atomic emission analytical zone. Reference numeral 98 generally designates the plume from the injected sample which provides an ionic emission analytical zone. Reference numeral 100 generally designates an after-discharge region which shows residual emissions from the hot gases and sample molecules. Depending upon the particular sample being introducted, each of these zones or regions may have a different color. For example, when the sample is yttrium, zone 96 will be pink, zone 98 will be blue, and region 100 will be red.

As will be appreciated from FIG. 3, the atomic and ionic emission zones are vertically separated or spaced such that the atomic emission analytical zone is below the ionic emission analytical zone. Both of these analytical zones are detectable by the DCP spectrometer's optical detection system generally designated by reference numeral 102. It should also be noted that both of these analytical zones provide relatively distinct areas which facilitate detection by the DCP spectrometer's optical detection system 102.

In order to illustrate the conical nature of the plasma created in accordance with the present invention, a portion of FIG. 3 has been enlarged in FIG. 4. In this regard, the shading lines are used to illustrate the fact that the individual plasma current trains 94 provided by the electrodes 12–16 combine to form a plasma body which has a conical underside. The apex or vertex of this cone is generally designated by the reference numeral 104. As shown by the cross-section of the plasma illustrated in FIG. 5, the current trains join together to form a plasma body 106 which is in the general form of an uninterrupted cone within the area of the dashed circle 108. The reference numeral 110 indicates the highly luminous region of high electron density in the current trains 112. The reference numeral 114 indicates the region of lower electron density which represent a visible hole created by the cooler aerosol sample penetrating the main plasma body.

In order to illustrate the analytical performance of the present invention, Table I below lists exemplary detection limits for the emission source 10 described above.

TABLE I

| Sample Element | Emission Wavelength Line (nm) | Detection Limit (ng/ml) |
|---|---|---|
| Calcium II | 393.3 | 0.9 |
| Calcium I | 422.6 | 8.0 |
| Magnesium II | 279.5 | 8.0 |
| Berrylium II | 313.0 | 6.5 |
| Strontium II | 407.7 | 0.4 |

The spectrometer apparatus and experimental conditions used in achieving these results are listed below in Table II.

TABLE II

| | |
|---|---|
| Spectrometer | Instruments SA, Inc., model JY38 spectrometer |
| Applied Voltage | 100 volts, D.C. |
| Running Current | 8 amp., D.C. |
| Argon flow rates | 2-3 Cathode (liters/min.) 2-3 Anodes (liters/min.) |
| Argon Pressure at Nebulizer | 20 psi |
| Argon flow rate at Nebulizer | 1 Liter per minute |
| Sample delivery rate | 1 Liter per minute |
| Optical detection slit opening setting | 25 Micron |

It will be appreciated that the above disclosed embodiment is well calculated to achieve the aforementioned objects of the present invention. In addition, it is evident that those skilled in the art, once given the benefit of the foregoing disclosure, may now make modifications of the specific embodiment described herein without department from the spirit of the present invention. Such modifications are to be considered within the scope of the present invention which is limited solely by the scope and spirit of the appended claims.

I claim:

1. A spectrochemical emission source, comprising:
at least three sources of an ionized gas plasma stream, each of said sources receiving D.C. electrical power such that one of said sources has the opposite polarity of the other of said sources;
means for supporting and aligning said sources such that the combination of said ionized gas plasma streams form a plasma body having a generally conical shape at one end of said plasma; and
means for injecting a sample stream into said plasma body such that said sample stream is captured by said conical shape of said plasma body and transmitted into said plasma body.

2. The spectrochemical emission source according to claim 1, wherein said supporting and aligning means comprises a base structure which circumferentially spaces said sources about a central axis such that the longitudinal axes of said sources converge radially toward said central axis at an acute angle to said central axis.

3. The spectrochemical emission source according to claim 2, wherein the longitudinal axes of each of said sources converge radially toward said central axis at substantially the same acute angle to said central axis.

4. The spectrochemical emission source according to claim 3, wherein the tips of each of said sources lie in a common plane, and each of said sources are substantially equally spaced from each other.

5. The spectrochemical emission source according to claim 2, wherein said base structure is also formed to support and align said sample stream injecting means.

6. The spectrochemical emission source according to claim 2, wherein said sample stream injecting means is concentrically aligned with said central axis, and said central axis is generally vertically disposed.

7. The spectrochemical emission source according to claim 1, wherein the injection of said sample stream creates an ionic emission analytical zone above said plasma body and an atomic emission analytical zone below said plasma body.

8. A DCP spectrometer emission source for creatng a high temperature plasma through which an aerosol sample stream is able to penetrate, comprising:
at least three electrodes, each of said electrodes having an electrode member and conduit means for conveying an ionizable gas passed said electrode members, said electrode members being connected to means for providing D.C. electrical power such that two of said electrode members have the same polarity and the third of said electrode members has the opposing polarity;
base means for circumferentially spacing said electrodes about a central axis such that the longitudinal axes of said electrode members converge radially toward said central axis at an acute angle to a plane which is perpendicular to said central axis; and
introduction means associated with said central axis for injectng said aerosol sample stream into the plasma created by said electrodes.

9. The DCP spectrometer emission source according to claim 8, wherein said electrodes create a plasma having a generally conical shape at one extremity thereof, and said aerosol sample stream is captured in said conical shape and transmitted into said plasma.

10. The DCP spectrometer emission source according to claim 9, wherein said central axis is generally vertically disposed and said plane is generally horizontally disposed.

11. The DCP spectrometer emission source according to claim 10, wherein said acute angle is between 15 and 60 degrees.

12. The DCP spectrometer emission source according to claim 11, wherein said acute angle is about 30 degrees.

13. The DCP spectrometer emission source according to claim 11, wherein said introduction means includes an introduction tube which is supported and substantially vertically aligned along said central axis by said base means.

14. The DCP spectrometer emission source according to claim 13, wherein said electrodes are mounted to said base means such that they are substantially equally spaced from each other.

15. The DCP spectrometer emission source according to claim 14, wherein one of said electrode members is a cathode and the other of said electrode members are anodes.

16. The DCP spectrometer emission source according to claim 15, wherein said introduction tube is formed with an outlet orifice having an internal diameter between 1 and 2 millimeters.

17. The DCP spectrometer emission source according to claim 10, wherein said base means includes a generally channel-shaped track which extends along a sloped surface of said base means for mounting said electrodes to said base means.

18. The DCP spectrometer emission source according to claim 17, wherein said base means is comprised of a central sleeve section which supports and aligns said introduction tube, and an outer platform section which provides said track along said sloped surface.

19. The DCP spectrometer emission source according to claim 13, wherein said introduction means also includes a nebulizer and a spray chamber interposed between said introduction tube and said nebulizer.

* * * * *